US00PP33200P3

(12) United States Plant Patent
Ponson et al.

(10) Patent No.: US PP33,200 P3
(45) Date of Patent: Jun. 29, 2021

(54) BLUEBERRY PLANT NAMED 'FLR12-89'

(50) Latin Name: ***Vaccinium corymbosum* L.**
Varietal Denomination: FLR12-89

(71) Applicant: Florida Foundation Seed Producers, Inc., Marianna, FL (US)

(72) Inventors: Sophie Ponson, Seville (ES); James W. Olmstead, Aptos, CA (US); Jean Clement Marcaillou, Seville (ES); Patricio R. Munoz Del Valle, Gainesville, FL (US); Jacques Kouadio, Seville (ES)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/923,952

(22) Filed: Jul. 8, 2020

(65) Prior Publication Data

US 2021/0015014 P1 Jan. 14, 2021

(30) Foreign Application Priority Data

Jul. 9, 2019 (EP) ..... 20191680

(51) Int. Cl.
*A01H 6/36* (2018.01)
*A01H 5/08* (2018.01)

(52) U.S. Cl.
USPC ..... Plt./157
CPC ..... *A01H 6/368* (2018.05)

(58) Field of Classification Search
USPC ..... Plt./157
See application file for complete search history.

(56) References Cited

U.S. PATENT DOCUMENTS

PP19,503 P3 11/2008 Lyrene

FOREIGN PATENT DOCUMENTS

EP 20191681 7/2019
EP 20191682 7/2019

OTHER PUBLICATIONS

U.S. Appl. No. 16/923,942, filed Jul. 8, 2020, Ponson et al.
U.S. Appl. No. 16/923,960, filed Jul. 8, 2020, Ponson et al.

*Primary Examiner* — Annette H Para
(74) *Attorney, Agent, or Firm* — Dentons US LLP

(57) ABSTRACT

'FLR12-89' is a new and distinct southern highbush blueberry (*Vaccinium corymbosum* L.) variety distinguished by a low chilling requirement, semi-upright growth habit, and large, firm fruit with a small, dry picking scar.

5 Drawing Sheets

Latin name of the genus and species of the plant claimed: *Vaccinium corymbosum* L.

Variety denomination: 'FLR12-89'.

CROSS REFERENCE TO RELATED APPLICATIONS

This application claims the benefit of European Community Plant Breeders Rights Appl. No. 20191680, filed Jul. 9, 2019, herein incorporated by reference in its entirety.

BACKGROUND OF THE INVENTION

The present invention relates to a new and distinct hybrid variety of southern highbush blueberry (*Vaccinium corymbosum* L.) named 'FLR12-89'. 'FLR12-89' is a blueberry clone distinguished by its low chilling requirement, very good performance when grown in an evergreen production system, very early ripening, and firm berries. Several thousand plants of 'FLR12-89' have been propagated and established in Lalla Mimouna, Morocco, and the resulting plants have all been phenotypically indistinguishable from the original plant.

'FLR12-89' originated as a seedling from a self-cross of 'Snowchaser' as the female (seed) parent and the male (pollen) parent. This cross was made in Lalla Mimouna, Morocco in 2012. The seedling was planted in a high-density field nursery in 2014 and the first fruit were evaluated during the same year. Due to its early fruit production and excellent fruit quality, 'FLR12-89' was selected and first asexually propagated in Lalla Mimouna, Morocco by softwood stem cuttings. In 2015, an experimental 10-plant test plot was established as part of a variety test at Lalla Mimouna Morocco. Based on the growth, yield, and fruit quality of this plot, 'FLR12-89' was repropagated by softwood stem cuttings and in 2016 experimental test plots were established at two other farms in Morocco. These plots have been observed during flowering and ripening each year, and no mutations or off-type plants have been observed.

'Snowchaser' (U.S. Plant Pat. No. 19,503) is an important southern highbush blueberry variety widely planted in the United States. 'FLR12-89' is believed to be most similar to 'Snowchaser'. Nonetheless, 'FLR12-89' and 'Snowchaser' are distinguishable at least in their fruit production, flower clusters, leaf shape, and leaf pubescence at the margins. Specifically, the claimed plant produces fruit five-to-six weeks earlier than 'Snowchaser'. The fruit of 'FLR12-89' is also consistently firmer than the fruit of 'Snowchaser' throughout the harvest season and plants of 'FLR12-89' produce roughly 18% more fruit than plants of 'Snowchaser' when grown in similar locations and under similar horticultural practices. Additionally, 'FLR12-89' exhibits tight flower clusters, and an elliptic leaf shape with an absence of leaf pubescence at the margins, while 'Snowchaser' exhibits medium to open flower clusters, and an ovate leaf shape with sessile glands along the margins of the leaf blade.

Similar to 'FLR12-89', 'FLR14-372' (U.S. Plant patent application Ser. No. 16/923,960) is another southern highbush blueberry variety that is both characterized by very early fruit ripening, and originated from 'Snowchaser' as the female (seed) parent. Nonetheless, plants of 'FLR12-89' and 'FLR14-372' can be readily and unambiguously distinguished from one another at least based upon their internode length, flower clusters, and berry characteristics. Specifically, 'FLR12-89' exhibits longer internode length, tight flower clusters, and berries having a smooth texture and lacking a strong aroma flavor, whereas 'FLR14-372' exhibits shorter internode length, medium flower clusters; and berries having a crunchy texture and a very strong aroma flavor. Also, plants of 'FLR12-89' display a growth habit that is more compact than plants of 'FLR14-372'.

SUMMARY OF THE INVENTION

Blueberry variety 'FLR12-89' exhibits outstanding and distinguishing characteristics when grown under normal horticultural practices in Lalla Mimouna, Morocco, including: (1) a very low chilling requirement; (2) very good performance as an evergreen plant; (3) very early fruit ripening; and (4) firm, medium-sized berries.

BRIEF DESCRIPTION OF THE DRAWINGS

The accompanying photographs show typical bush, flower, and fruit characteristics for 'FLR12-89'. Colors shown are as true as can be reasonably reproduced by photographic procedures and may differ from those cited in the detailed description, which accurately describes the colors of 'FLR12-89'.

DETAILED BOTANICAL DESCRIPTION

Figure 1:
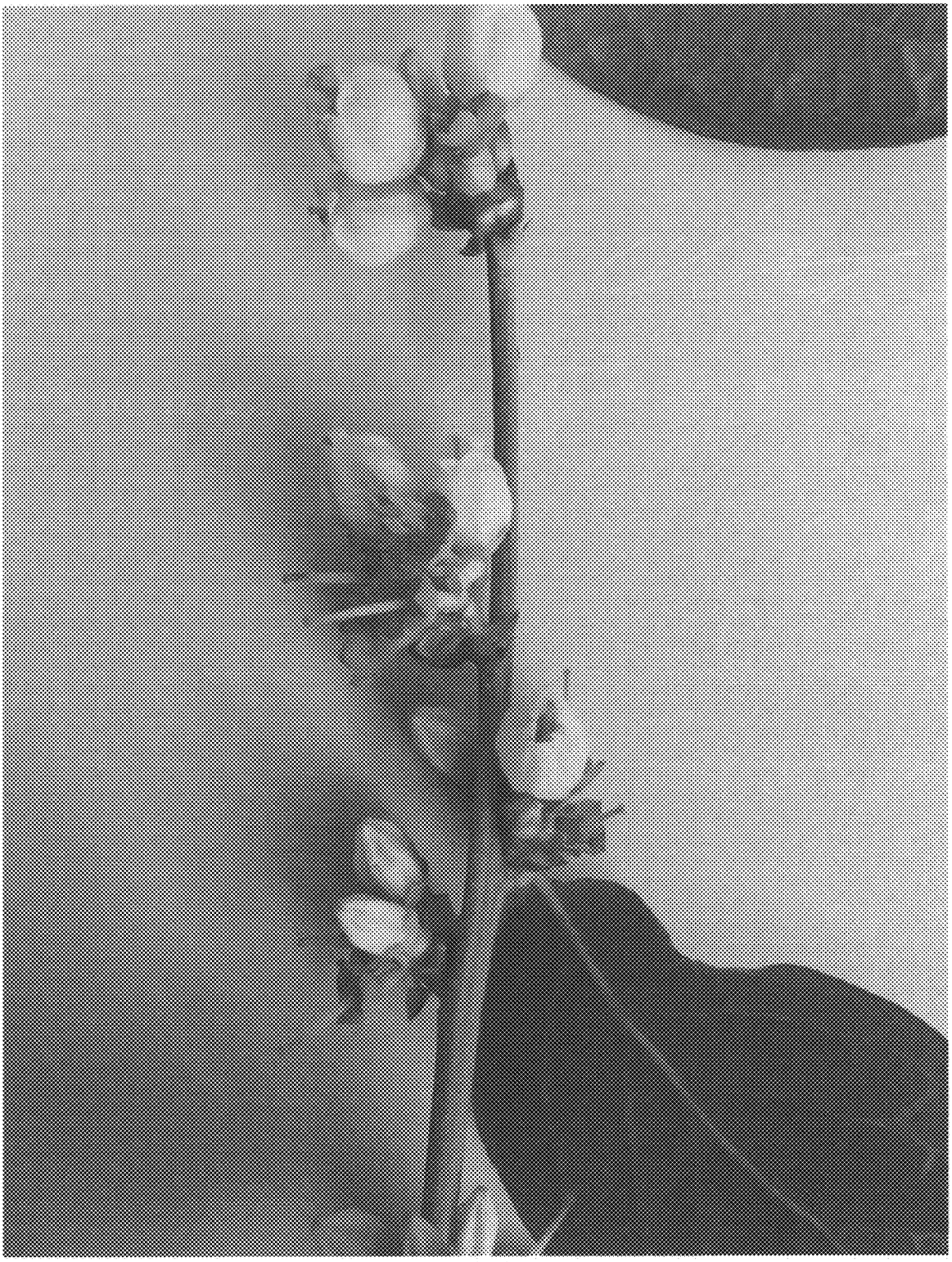
FIG. 1—Shows several clusters of flowers of 'FLR12-89', as observed during the early stages of flowering.
Figure 2:
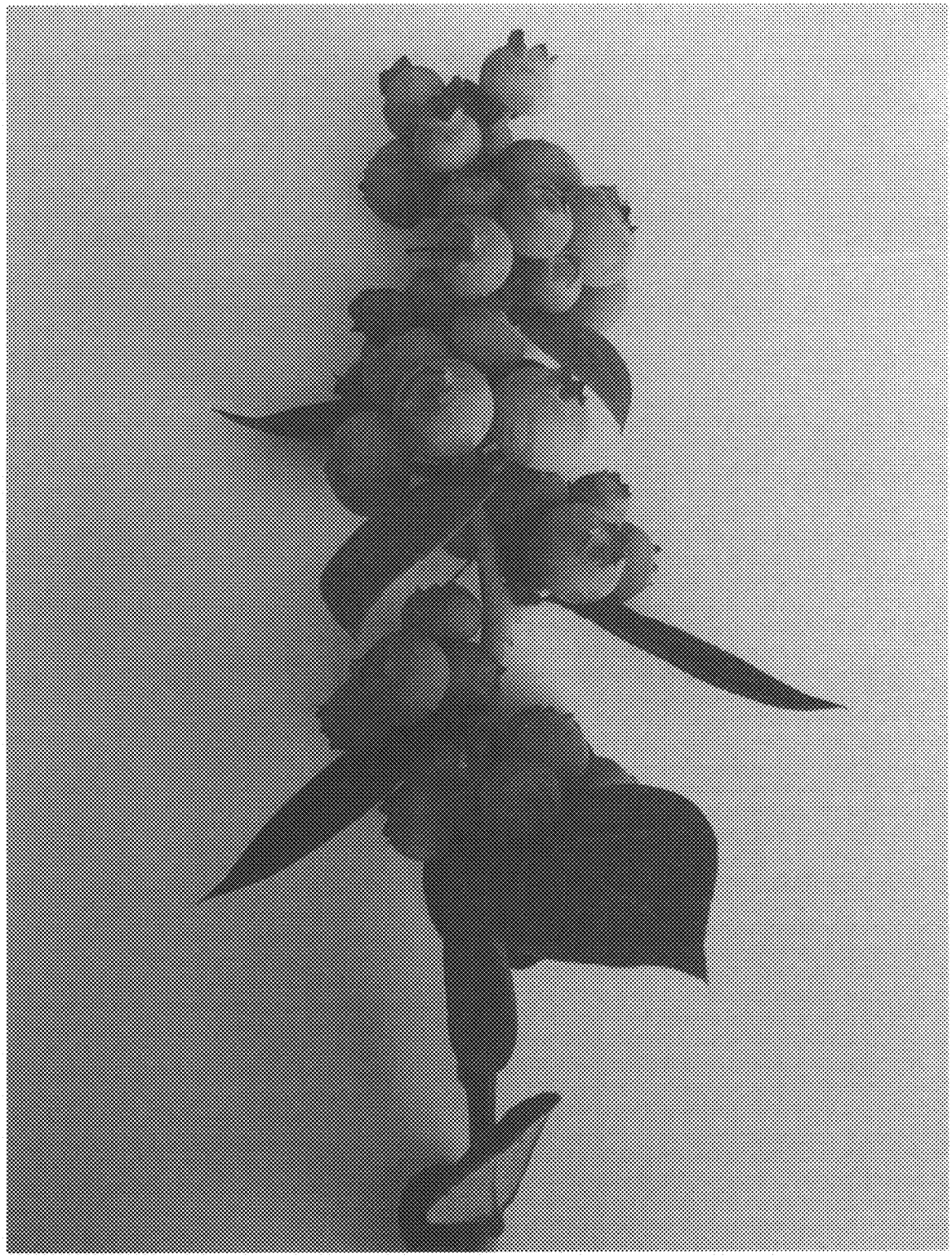
FIG. 2—Shows branches with green fruit of 'FLR12-89' during the fruit ripening period.
Figure 3:
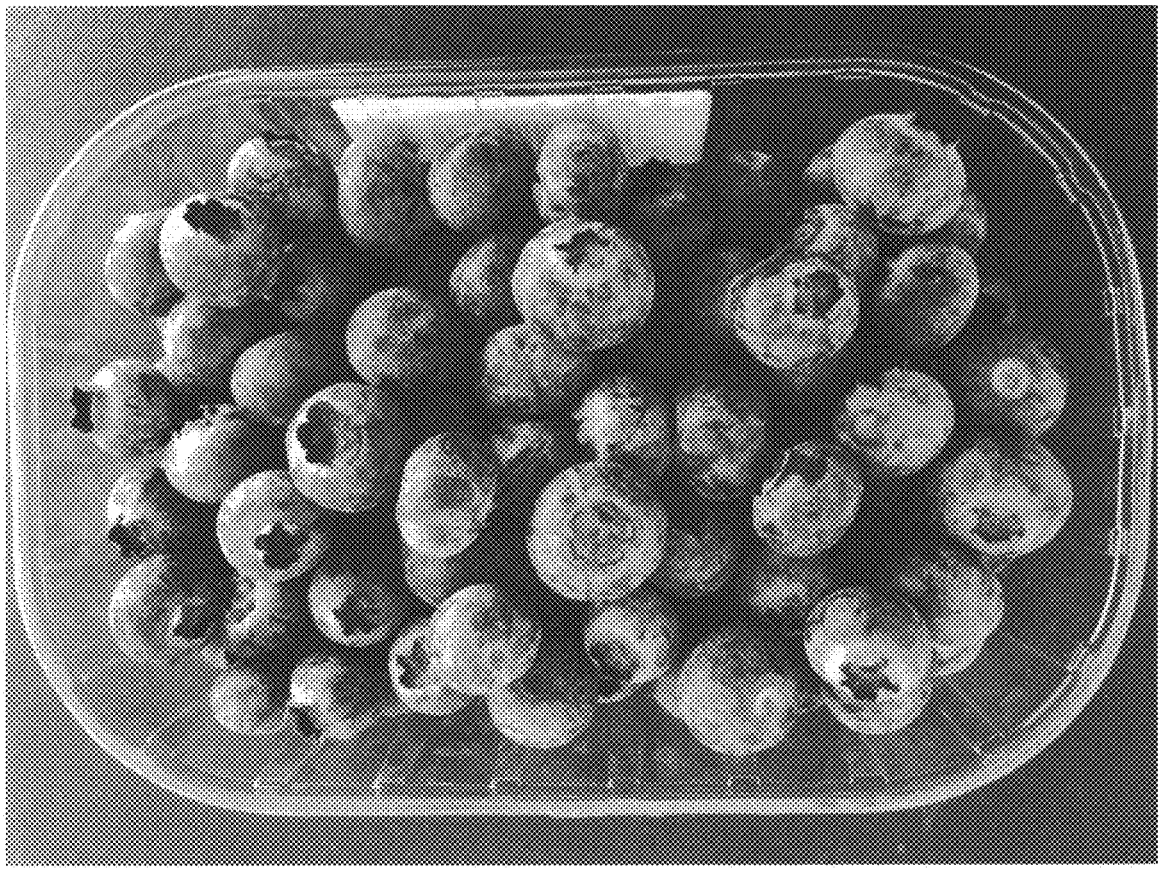
FIG. 3—Shows a close-up of ripe harvested 'FLR12-89' berries.
Figure 4:
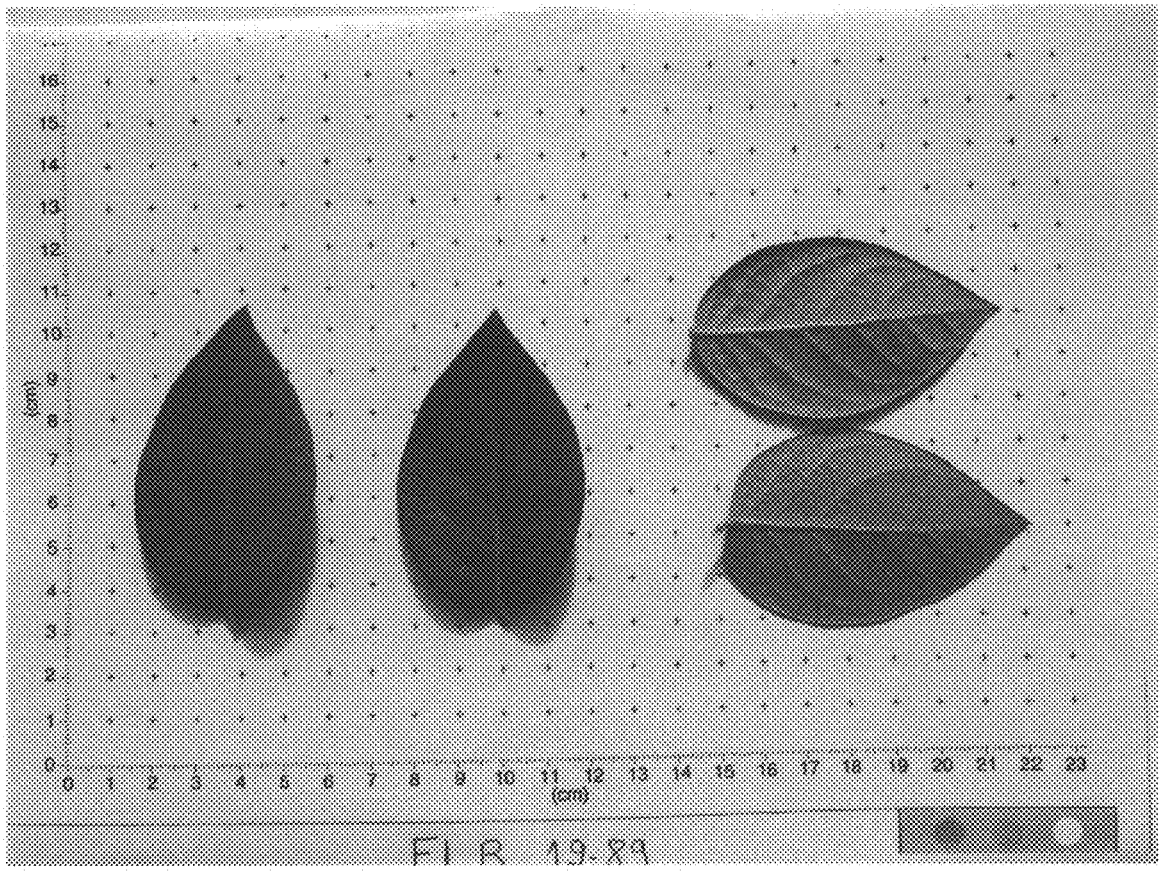
FIG. 4—Shows a close-up of mature 'FLR12-89' leaves with a scale bar.
Figure 5:
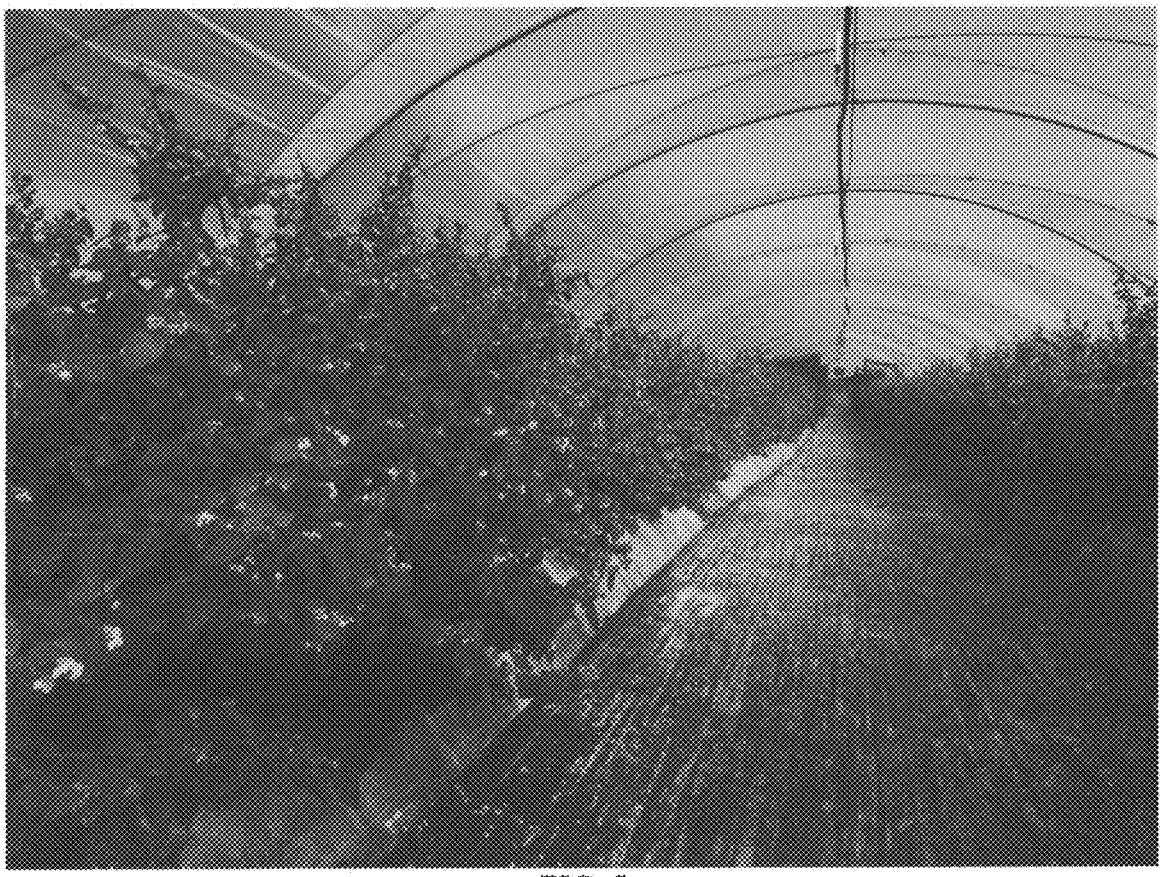
FIG. 5—Shows several 'FLR12-89' plants when grown in an evergreen production system in Lalla Mimouna, Morocco.

The following detailed description sets forth the distinctive characteristics of 'FLR12-89'. The data that define these characteristics were collected from asexual reproductions carried out in Morocco. The plants were 2 years of age when the data was collected. Certain characteristics may vary with plant age. 'FLR12-89' has not been observed under all possible environmental conditions, and the measurements given may vary when grown in different environments. Where means are given, the sample size was 10. Color descriptions are based on The Royal Horticultural Society (R.H.S.) Colour Chart by The Royal Horticultural Society, London, Fifth Edition, 2007. When The R.H.S. Color designations differ from the accompanying photographs, the R.H.S. color designations are accurate.

PHENOTYPIC DESCRIPTION OF *VACCINIUM CORYMBOSUM* L. ('FLR12-89')

Plant:

*Plant vigor*.—Medium.

*Growth habit*.—Compact semi-upright.

*Flower bud density (number) along flowering twigs in March*.—Medium to High, averaging 11.6.

*Twigginess*.—High.

*Tendency toward evergreenness*.—High.

*Productivity*.—In trials in Morocco, 'FLR12-89' was very productive, with higher total yields than 'Snowchaser'.

*Chilling requirement*.—'FLR12-89' has performed best under evergreen production conditions where chilling is not calculated. 'FLR12-89' flowered and leafed well in areas receiving an average of 300 chill hours (0 to 7° C.).

*Cold hardiness*.—'FLR12-89' has not been grown in temperate climates with extremely cold winter temperatures. Plants have survived winter freezes of −2° C. without damage.

*Ease of propagation*.—In propagation by cuttings of softwood stems, 'FLR12-89' has a good percentage of rooting (85% success), superior to 'Snowchaser'. 'FLR12-89' has also a very good response to meristematic culture.

Trunk and branches:

*Suckering tendency*.—High. Plants typically average 13.0 canes (with observed number of canes ranging from a minimum of 9 to a maximum of 16) arising from crown.

*Surface texture (of strong, 6-month-old shoots observed in March)*.—Smooth.

*Surface texture (of 3-year-old and older wood)*.—Rough.

*Color of new twigs observed in the field*.—Yellow-green N144D.

*Color of 3-year-old, rough-textured canes*.—Greyed-brown N199C.

*Internode length (strong, upright shoots measured in March)*.—Mean of 38.0 mm.

Leaves:

*Length (including petiole, from tip of petiole to end of blade)*.—Mean of 7.5 cm.

*Width (at widest point)*.—Mean of 4.1 cm.

*Shape*.—Elliptic.

*Margin*.—Entire.

*Color*.—Upper surface: Green N137B. Lower surface: Yellow-green N147B.

*Pubescence*.—Upper surface of leaves: Absent. Lower surface of leaves: Absent. Margins: Absent.

*Relative time of leafing versus flowering*.—When grown as an evergreen plant, leafing is after flowering.

Flowers:

*Arrangement*.—Flowers are arranged alternately along a short, leafless, deciduous branch.

*Fragrance*.—Strong floral fragrance.

*Shape*.—Urceolate.

*Flowering period*.—'FLR12-89' has 2 blooms: the first is early and spread from September to November (between 4 to 7 weeks before 'Snowchaser'), and the second from January to February.

*Cluster* (*tight, medium, loose*).—Tight.

*Number of flowers per cluster*.—Mean of 8.3.

*Pedicel*.—Length at time of anthesis: Mean of 10.5 mm. Color at time of anthesis: Yellow-green 144C.

*Peduncle*.—Length at time of anthesis: Mean of 16.3 mm. Color at time of anthesis: Yellow-green 144C.

*Calyx*.—Surface texture: Smooth. Diameter: Mean of 7.2 mm. Color (outer surface, visible at the time of anthesis without removing the corolla tube): Green 138C.

*Corolla*.—Diameter: Mean of 8.6 mm. Length (from pedicel attachment point to corolla tip excluding the pedicel): Mean of 9.0 mm. Aperture diameter: Mean of 4.9 mm. Texture: Smooth. Color: White 155B.

Reproductive organs:

*Style*.—Length (top of ovary to stigma tip): Mean of 9.0 mm. Color: Yellow-green 145B. Location of tip of stigma relative to lip of the corolla — Stigma tip is approximately even to 1 mm outside the corolla lip.

*Anthers*.—Color: Greyed-orange N167B. Pollen — Abundance of shed: Low to Medium. Color: Orange-white 159B.

*Self-fruitfulness*.—Low to Medium. Planting in field configurations that promote cross fertilization with other southern highbush varieties is recommended for all southern highbush blueberry plants.

Fruit:

*Mean date of* 50% *harvest in Lalla Mimouna, Morocco*.—January 31.

*Diameter of calyx aperture on mature berry*.—Mean of 8.9 mm.

*Size and shape of calyx lobes on mature berry*.—Small, flat. Medium calyx basin.

*Pedicel length on ripe berry*.—Mean of 9.8 mm.

*Detachment force for ripe berries* (*easy, medium, hard*).—Medium.

*Number of berries per cluster*.—Mean of 8.1.

*Fruiting type*.—On one-year-old and current season's shoots.

Berry:

*Cluster* (*tight, medium, loose*).—Tight.

*Weight* (*on well-pruned plants*).—Mean of 1.6 grams.

*Height*.—Mean of 14.4 mm.

*Width*.—Mean of 19.0 mm.

*Shape*.—Oblate.

*Surface color of mature berries ripe on the plant*.—Violet-blue 98D.

*Surface color of ripe berry after polishing*.—Black 203B.

*Immature berry color, with bloom*.—Greyed-green 193B.

*Immature berry color without bloom*.—Yellow-green N144C.

*Surface wax*.—Medium to high. The surface wax on 'FLR12-89' has only moderate persistence.

*Pedicel scar*.—Small and dry. Mean of 3.7 mm.

*Firmness*.—Firm.

*Flavor*.—Good balance between sweetness and acidity.

*Texture*.—Smooth.

Seeds:

*Color of dried seeds*.—Greyed-orange 165A.

*Length of well-developed dried seed*.—Mean of 2.0 mm.

*Width of well-developed dried seed*.—Mean of 1.0 mm.

Use: 'FLR12-89' produces southern highbush blueberries suitable for fresh markets. 'FLR12-89' has performed best in trials when grown under an evergreen management system.

Resistance to diseases, insects, and mites: 'FLR12-89' has grown vigorously and shows excellent bush survival when grown under protected cultivation in an evergreen management system. 'FLR12-89' can under certain conditions be sensitive to root rot (*Phytophthora cinnamomi*). 'FLR12-89' appears to have excellent resistance to the fungal species that cause summer leaf spots.

What is claimed is:

1. A new and distinct variety of southern highbush blueberry plant named 'FLR12-89', as illustrated and described herein.

* * * * *